(12) United States Patent
Gerhardt et al.

(10) Patent No.: US 9,383,322 B2
(45) Date of Patent: Jul. 5, 2016

(54) KIT CONTAINING SEALING LIQUID FOR SAFETY CLOSURES

(71) Applicant: FRANCOTYP-POSTALIA GMBH, Birkenwerder (DE)

(72) Inventors: Thomas Gerhardt, Berlin (DE); Wolfgang Muhl, Hohen Neuendorf (DE)

(73) Assignee: Fracotyp-Postalia GmbH, Birkenwerder (DE)

( * ) Notice: Subject to any disclaimer, the term of this patent is extended or adjusted under 35 U.S.C. 154(b) by 282 days.

(21) Appl. No.: 14/089,813

(22) Filed: Nov. 26, 2013

(65) Prior Publication Data

US 2014/0076042 A1    Mar. 20, 2014

Related U.S. Application Data

(60) Continuation-in-part of application No. 13/242,527, filed on Sep. 23, 2011, now Pat. No. 8,951,382, which is a division of application No. 11/807,560, filed on May 29, 2007, now abandoned.

(30) Foreign Application Priority Data

May 29, 2006    (DE) .................. 10 2006 025 200

(51) Int. Cl.
| | |
|---|---|
| *G01N 21/84* | (2006.01) |
| *C09J 11/06* | (2006.01) |
| *C09J 11/08* | (2006.01) |
| *B43M 5/00* | (2006.01) |
| *B43M 7/00* | (2006.01) |
| *G09F 3/03* | (2006.01) |
| *G07B 17/00* | (2006.01) |

(52) U.S. Cl.
CPC ................ *G01N 21/84* (2013.01); *B43M 5/00* (2013.01); *B43M 7/00* (2013.01); *C09J 11/06* (2013.01); *C09J 11/08* (2013.01); *G07B 17/00193* (2013.01); *G09F 3/03* (2013.01)

(58) Field of Classification Search
CPC ....................................... G01N 21/84
USPC ........................ 73/150 R; 156/325
See application file for complete search history.

(56) References Cited

U.S. PATENT DOCUMENTS

| | | | |
|---|---|---|---|
| 4,815,654 A | 3/1989 | Buescher | |
| 5,554,842 A * | 9/1996 | Connell | .................. B07C 3/18 |
| | | | 106/31.32 |
| 5,837,042 A * | 11/1998 | Lent | ....................... B41M 3/144 |
| | | | 106/31.14 |

(Continued)

FOREIGN PATENT DOCUMENTS

| | | |
|---|---|---|
| DE | 2319866 A1 | 11/1974 |
| DE | 3431239 A1 | 7/1985 |

(Continued)

*Primary Examiner* — Daniel Lee
(74) *Attorney, Agent, or Firm* — Laurence A. Greenberg; Werner H. Stemer; Ralph E. Locher (57) ABSTRACT

A sealing liquid for sealing mail pieces contains water and a penetration agent. The sealing liquid is applied by letter-closing devices and franking machines containing such a sealing liquid. Once sealed, the opening of the letter produces a pronounced pattern so that it is clear that the letter has been opened. Therefore any attempts to reseal the once opened enveloped are easily detected.

10 Claims, 6 Drawing Sheets

(56) References Cited

U.S. PATENT DOCUMENTS

| | | | |
|---|---|---|---|
| 6,322,663 B1 * | 11/2001 | Muller | B43M 5/042 156/441.5 |
| 6,551,391 B1 | 4/2003 | Gerhardt et al. | |
| 7,384,500 B2 | 6/2008 | Luedtke | |
| 2001/0003396 A1 | 6/2001 | Farren | |
| 2004/0038385 A1 | 2/2004 | Langlois et al. | |
| 2005/0208109 A1 * | 9/2005 | Houtan | B43M 11/06 424/443 |

FOREIGN PATENT DOCUMENTS

| | | |
|---|---|---|
| DE | 8716046 U1 | 12/1988 |
| DE | 4436294 A1 | 4/1996 |
| DE | 202004011390 U1 | 10/2004 |

* cited by examiner

KIT CONTAINING SEALING LIQUID FOR SAFETY CLOSURES

CROSS-REFERENCE TO RELATED APPLICATION

This is a continuation-in-part application of U.S. patent application Ser. No. 13/242,527, filed Sep. 23, 2011, which was a divisional application of U.S. patent application Ser. No. 11/807,560, filed May 29, 2007; the application also claims the priority, under 35 U.S.C. §119, of German patent application No. DE 10 2006 025 200.4, filed May 29, 2006; the prior applications are herewith incorporated by reference in their entireties.

BACKGROUND OF THE INVENTION

Field of the Invention

The invention relates to a sealing liquid, in particular for sealing mail pieces, containing water, to the uses of such a sealing liquid for safety closures, to letter-closing devices and franking machines containing such a sealing liquid, and to a method for the detection of unauthorized opening of a mail piece. The invention relates moreover to a kit for the detection of unauthorized opening of a mail piece containing at least one sealing liquid which contains a non-visible safety additive and device for application of such sealing liquid to a mail piece, which is shaped in a way that a defined lateral inhomogeneous distribution of the safety liquid will be achieved and device for the visualization of the safety additive.

Mail pieces, in particular letters, in big quantities are in most cases automatically sealed and franked by the sender. For this purpose, amongst others, closing devices and franking machines are used, wherein both components are often connected with each other and sometimes form structural units. As an example, reference is made to German Utility Model DE 20 2004 011 390 U1.

In connection with the sealing of mail pieces, the sealing flaps of which are provided with a gumming, it is necessary to wet the gum before sealing. For this purpose, a sealing liquid is (automatically) applied to the gum by a wetting sponge. Then immediately after wetting the sealing flap is folded and pressed against an opposed surface of the mail piece envelope, and thus the mail piece is sealed.

From the practice, different sealing liquids are known. These are typically water or aqueous solutions, which on the one hand may contain biocides and fungicides, in order to prevent the occurrence of germ colonies and unpleasant odors. On the other hand, a wetting agent may be added.

Thus sealed mail pieces are normally opened by a letter opener or the like, i.e. the mail piece is slit open in the area of an edge, and the contents is then taken out. However, a person, who is not authorized for opening, can open such a mail piece for instance by watering it or by exposing it to a water vapor-containing atmosphere. Then the adhesive of the gumming will be dissolved in the water depositing in the area of the adhesion and the sealing flap can be lifted. The unauthorized person can then inspect the contents of the mail piece and thereafter re-close the mail piece with contents by folding and pressing-down the sealing flap. With careful operations, the authorized person later receiving the mail piece cannot easily find out that before an unauthorized opening of the mail piece has been performed. This is disturbing for obvious reasons.

From published, non-prosecuted German patent application DE 4436294 A1 a sealing liquid is known in the art, which contains, besides the main component water, a second component of a two-component adhesive. The first component of the two-component adhesive is contained in the gumming.

From published, non-prosecuted German patent applications DE 3431239 A1 and DE-G 8716046, a safety letter envelope or a safety label is known in the art, wherein adhesive sections are disposed such that with (unauthorized) opening an irreparable destruction of the label or of the letter envelope will take place, which then can easily be identified.

From the laid open German patent application DE-OS 2319866, an enveloping machine with a wetting device is known in the art.

BRIEF SUMMARY OF THE INVENTION

It is the technical object of the invention to provide a sealing liquid, which is suitable for safety closures, i.e. reveals an unauthorized opening.

The invention is furthermore based on the technical problem, to provide a kit for the detection of unauthorized opening of a mail piece, including a sealing liquid which may be applied and detected with simple measures, without the need for an automatic device.

For achieving the technical object, the invention teaches a sealing liquid for sealing mail pieces containing water and a safety additive not being visible by immediate observation.

For achieving the technical object, the invention teaches furthermore a kit for the detection of unauthorized opening of a mail piece. The kit contains:

at least one sealing liquid for sealing mail pieces containing water and a safety additive not being visible by immediate observation, at least one device for application of the sealing liquid to a mail piece, the device being formed in a way, that a defined lateral inhomogeneous distribution of the sealing liquid will be achieved, and at least one device for the visualization of the safety additive.

The term immediate observation means the observation by a person without using technical means. In contrast, the safety additive can be made visible and/or detected by using technical means. It is therefore not a safety feature being visible with the naked eye.

The means for application of the sealing liquid to a mail piece may be a roller, a stamp or a sponge. The means may be formed in a way that it contains a surface structure. This surface structure may be in the form of a geometrical pattern (e.g. squares, diamonds, triangles, hexagons, but also line patterns, e.g. straight or curved lines or wave shaped pattern).

The invention is based on first experiments with a sealing liquid stained by a visible dye and the finding that by the automatic wetting of a gumming, the wetting will not take place laterally homogeneously, but a pattern will be formed because of the surface structure of the wetting sponge. Furthermore, it was detected that such a pattern will be destroyed by exposure to water vapor by flowing-out or washing-out processes. From this, the technical teaching of the invention originates, namely to provide a sealing liquid, the lateral distribution of which cannot easily be detected by the human eye, can however be made visible with technical means visible and/or detected with technical means. Then, based on the lateral distribution of the sealing liquid or of the safety additive, it can be found out, whether the safety additive has for instance been destroyed by heat and/or has been washed out. If this is detected, this is a sign of an unauthorized opening. If however the detected lateral distribution of the sealing liquid of the safety additive corresponds to a given lateral reference distribution (namely a lateral distribution, such as produced by wetting), then an unauthorized opening can be excluded, at least by dissolving the gumming.

The lateral distribution of the sealing liquid and thus of the safety additive can be arranged in the most different ways when sealing the mail piece. In the simplest case, the lateral distribution of the sealing liquid corresponds to a pattern, such as produced by placing the wetting sponge on the gumming or on the mail piece. It is however also possible that the wetting sponge or other means for applying the sealing liquid on the gumming or on the mail piece is configured such that the sealing liquid is applied with a given pattern, one-dimensional or two-dimensional. Simple one-dimensional patterns are for instance a sequence of sections, where sealing liquid is applied, and sections, where no sealing liquid is applied. The sequence suitably extends in the direction of the longitudinal extension of the gumming. This can for instance be put into practice by a wetting roller, which has, similar to a stamp, sections, which do not come into contact with the gumming or the mail piece. If such a roller having depressions and elevations along its periphery is wetted and rolled over the gumming, then a one-dimensional pattern is formed in the direction of the longitudinal extension of the gumming.

Correspondingly, a two-dimensional pattern can also be formed, and in this case the means for applying the sealing liquid have corresponding depressions and elevations in different directions. Two-dimensional patterns may be simple, for instance checkered, or also more complicated. In the latter case, a result similar to a water-mark is obtained.

Another example is a simple roller which contains a surface pattern and which may be wetted with the sealing liquid (e.g. by rolling on a sponge or ink-pad containing the sealing liquid and the sealing liquid may be applied by manual rolling over the gummed area of the mail piece). As an alternative, the means for the application of the sealing liquid may be a sponge, which by its unique pore structure will create a two-dimensional pattern which is by its very nature erratic.

Preferably, the safety additive is selected from the group containing "luminescent substances, peptides, proteins, nucleic acids, preferably with 2 to 50 nucleotides, low-molecular inorganic or organic substances different from other components of the sealing liquid".

A luminescent substance contains atoms, molecules or particles, which are suitable for luminescence. The term luminescence designates the emission of electromagnetic radiation, in particular in the IR, visible or UV range during a relaxation of an atomic or molecular electronic system from an excited state into a ground state. Hereby, the previous excitation can be performed by electric energy or an electric potential (electroluminescence), bombardment with electrons (cathodoluminescence), bombardment with photons (photoluminescence), heat effects (thermoluminescence) or friction (triboluminescence). The luminescence in particular contains the phosphorescence and the (photo)fluorescence. The fluorescence is a radiating deactivation of excited states, the transition from the excited state into the ground state being spin-permitted. The retention time in the excited state is typically approximately $10^{-8}$ s, i.e. the emission of the fluorescence radiation ends immediately after the end of the energy supply for the excitation. The phosphorescence is however a spin-forbidden deactivation of excited states by intercombination processes. Therefore, the relaxation is weak and slow. The retention time in an excited state is several milliseconds to hours and correspondingly long is the emission of the phosphorescence radiation. The emission wavelength of a luminescent substance is characteristic for the used dye and is determined by the energy difference between excited state and ground state, as the emission wavelength is designated the maximum of the emission intensity in an emission spectrum. Preferably, the luminescent substances are fluorescent dyes. With respect to suitable fluorescent dyes, reference is exemplarily made to international patent disclosure WO 03/052025 A (corresponding to U.S. Pat. No. 7,699,456), international patent disclosure WO 02/053677 A (corresponding to U.S. Pat. No. 8,241,765), published, European patent application EP 0147252 A, British patent GB 2,258,659 and F. M. Winnik et al., Xerox Discloser Journal Vol. 17, No. 3, 1992, pages 161-162. Suitable fluorescent dyes on an organic base, for instance naphthalimide, coumarine, xanthene, thioxanthene, naphtholactame, azlactone, methine, oxazine, or thiazine, are known from the literature, for which purpose reference is exemplarily made to Schwander et al., "Fluorescent Dyes" in Ullmann's Encyclopedia of Industrial Chemistry, Wiley-VCH Verlag GmbH & Co. KGaA, 2002. With respect to suitable fluorescence-conjugated polymers, reference is complimentarily made to the documents McQuade et al., Chem. Rev. 100:2537-2574 (2000), Yang et al., J. Am. chem. Soc. 120:11864-11873 (1998), Yang et al., J. Am. Chem. Soc. 120:5321-5322 (1998) and Zhou et al., J. Am. Chem. Soc. 117:12593-12602 (1995). Fluorescent dyes may also be differently doped, for instance with europium, whereby then different emission wavelengths are obtained. As examples only for suitable luminescent substances, the substances of the Luminex range of the company AlliedSignal are mentioned here. Luminescent substances according to the invention have a color, which when viewed under daylight cannot easily be detected. Alternatively, the luminescent substances, if they comprise a color, are so strongly diluted that the color cannot easily be detected. The detection of a luminescent substance is performed by excitation with a suitable primary radiation and detection of the emission radiation excited thereby. A spatially resolved detection is for instance possible by a CCD camera and a suitable optical system. A linear CCD element may be used in the case of a one-dimensional pattern, and in this case the longitudinal extension of the gumming and the line of the sensor elements should approximately be optically parallel. However, for two-dimensional patterns, a two-dimensional CCD array with a suitable optical system may also be used, which then permits an immediate reproduction and representation of the detected pattern.

In principle, proteins or peptides of any species can be used, and these are preferably non-toxic. Corresponding considerations apply to the nucleic acids. For a sealing liquid, preferably only a single species should be used, i.e. always identical molecules. The detection of a protein or peptide may for instance be made by an antibody being specific for the peptide or protein. If necessary, the protein or peptide is first immobilized and then incubated with the antibodies. By use of dyes coupled to such an antibody then a pattern can be made immediately visible for the human eye, analogous to the staining of a tissue cut in biochemistry. However, antibodies may also be used, to which luminescent substances are coupled, which are then made visible by irradiation for instance with UV light. In the case of the nucleic acids, molecules of any species may be used, too. The detection takes place for instance by usual methods of the hybridization of detector nucleic acids, which are specific for the nucleic acids used in the sealing liquid, i.e. hybridize therewith under stringent conditions, that is, are at least partially complementary in the sequence. The detector nucleic acids then either carry dyes, which are easily recognizable, or it is also possible to use luminescent substances coupled to the detector nucleic acids and to detect them in the mentioned way. In the relevant literature of biochemistry the different methods for the spatially resolved detection of peptides, proteins or nucleic acids can be found, so that reference is made thereto.

Low-molecular organic or inorganic substances have a molecular weight of typically below 5,000 Da, in particular below 1,000 Da. In particular can be used substances, which can be detected by characteristic chemical reactions with an analysis substance in a simple and spatially resolved manner. Examples are salts of rather rare elements, such as for instance Pd, Pt, Ir, Au or Ag.

The detection of the safety additive is performed for all variants with an at least one-dimensional spatial resolution.

A sealing liquid according to the invention may preferably contain the following components: a) 50 to 99.9, preferably 70 to 99.0, in particular 80 to 99.0 wt.-% water, b) 0 to 10.0, preferably 1.0 to 30.0, in particular 1.0 to 20 wt.-% penetration agent, c) 0 to 10.0, preferably 0 to 3.0, in particular 0.01 to 1.0 wt.-% wetting agent, d) 0 to 10.0, preferably 0 to 3.0, in particular 0.01 to 2.0 wt.-% stabilizer and/or buffer, e) 0 to 5.0, preferably 0 to 2.0, in particular 0.01 to 1.0 wt.-% dyes, f) 0 to 5.0, preferably 0 to 1.0, in particular 0.01 to 0.1 wt.-% aromatic substances, g) 0 to 10.0, preferably 0 to 1.0, in particular 0 to 0.1 wt.-% biocides and/or fungicides and/or other usual auxiliary substances, h) 0.0001 to 10.0, preferably 0.0001 to 2.0, in particular 0.0001 to 0.1 wt.-% safety additive, and the components a) to h) always add up to 100 wt.-%.

With respect to the facultatively present components b) to g), which are always different from the component h), the following is set forth.

A penetration agent is a substance, which leads to an absorption time of the sealing liquid in paper materials being reduced compared to water, in particular by at least 10%, preferably by at least 20%, most preferably by at least 50%, referred to the absorption time of pure water. Wetting agents and penetration agents are different in the terminology used here. The absorption time is measured as the time, in which a drop of the sealing liquid having a volume of 100 µl±5 µl applied onto the paper material has completely penetrated the paper. The measurement of the absorption time, also called penetration time, is known from the ink jet technology, and as an example, reference is made to the published, European patent application EP 1072653 A2 (corresponding to U.S. Pat. No. 6,551,391). Suitable penetration agents are for instance C1-8 alkyl esters of C1-8 monocarbonic, dicarbonic, or tricarbonic acids, wherein the carbonic acid may be OH-substituted, in particular in the a position. The carboxyl groups may completely or partially be esterd. Other preferred penetration agents are C1-8 ethers von C1-8 polyols, wherein at least one OH group of the polyol is not ethered. As polyols in particular diols or triols may be used, and in the latter case 1 or 2 OH groups may be ethered. C1-8 alkyl may be linear, branched, saturated or unsaturated. As C1-8 alkyl for instance methyl, ethyl, propyl, isopropyl, butyl, isobutyl, tert-butyl, pentyl etc may be used. C1-8 carbonic acids may be linear or branched, saturated or unsaturated. As C1-8 carbonic acids may be used formic acid, acetic acid, propionic acid, butyric acid, valerianic acid, capronic acid, isobutyric acid, isovalerianic acid, acrylic acid, crotonic acid etc. As hydroxycarbonic acids for instance glycolic acid, lactic acid, mandelic acid, malic acid, tartaric acid and citric acid may be used. As diols for instance 1,2-ethanediol, 1,3-propanediol, 1,2-propanediol, 1,4-butanediol, 1,3-butanediol, 1,2-butanediol, etc may be used. The polyol may contain one or more ether groups. An example for such a polyol is 2,2'-oxydiethanol (diethylene glycol). As suitable specific compounds, the following are named non-exclusively: methyl lactate, ethyl lactate, propyl lactate, isopropyl lactate, malic acid diester, malic acid monoester, tartaric acid diester, tartaric acid monoester, ethylene glycol monomethylether, ethylene glycol monoethylether, ethylene glycol monopropylether, ethylene glycol monobutylether, diethylene glycol monomethylether, diethylene glycol monoethylether, diethylene glycol monopropylether, diethylene glycol monobutylether. With regard to further suitable penetration agents, as examples, reference is made to the published, European patent application EP 1072653 A (corresponding to U.S. Pat. No. 6,551,391) and the documents cited therein, as well as to the documents DE 69628897 T2 (corresponding to U.S. Pat. No. 5,674,314).

As wetting agents, for instance tensidic wetting agents are suitable. The wetting agent can be selected from the group containing non-ionic tensides, amphoteric tensides, anionic tensides, cationic tensides, and ricinoleic amino propyl betaine. Preferably they are biologically decomposable tensides. Preferably amphoteric tensides are used, since thereby surprisingly a particularly good wetting of the gum is achieved.

Further, a sealing liquid may contain one or more of the following additional and/or auxiliary substances: stabilizers and/or buffers, dyes, and/or aromatic substances. Of course, biocides (for instance Parmetol A6 or cetyltrimethylammonium bromide) and/or fungicides may also be added in a usual manner. As dyes and aromatic substances preferably substances having an approval as food additives are used, such as food colors, citral, hexyl hexonate etc. Stabilizers and/or buffers stabilize components of the sealing liquid, which can be hydrolyzed. For instance, Na lactate is a suitable stabilizer or buffer for lactate esters. As stabilizers or buffers in particular all usual set-up salts can be used, such as Na lactate, NaCl, KCl etc.

It is important for the understanding of the invention that the safety additive is no otherwise usual component of a sealing liquid, but is exclusively and only used for detection purposes. A safety additive has no other function for a mail piece envelope wetted therewith. In particular, a safety additive does not functionally correspond to one of the components b) to g) or to a component of a multi-component adhesive.

The invention further relates to the use of the above described sealing liquid to close mail pieces and to execute a method for producing a sealed mail piece wherein a flap provided with a gumming of a mail piece envelope including the mail piece or a section of the mail piece opposite to the folded flap is wetted with the sealing liquid with a defined laterally inhomogeneous distribution of the safety additive, and wherein the flap is then folded and pressed against an opposed surface of the mail piece envelope. The term laterally inhomogeneous distribution means a non-uniform distribution of the sealing liquid or of the safety additive, referred to the plane of the gumming or the opposed section of the mail piece envelope. In other words, the sealing liquid or the safety additive is applied with a pattern. The inhomogeneity will in the simplest case be such that the sealing liquid is applied in some sections, however not applied in other sections. It is however in principle also possible that different amounts or concentrations of safety additive according to the given pattern are applied.

The mail piece may in particular be a letter, and the mail piece envelope may be a letter envelope. It is preferred that the wetting and the folding and pressing-down of the flap is performed in an automatic manner in a letter-closing device.

The invention further relates to a letter-closing device containing a tank with a sealing liquid according to the invention, and having a wetting arm, which is provided for discharging sealing liquid from the tank and transferring discharged sealing liquid on the gumming or on a section with folded flap being opposite to the gumming of a mail piece inserted into the letter-closing device with a defined laterally inhomogeneous distribution of the sealing liquid or of the safety additive.

The invention further relates to a franking device having a letter-closing device according to the invention.

Subject matter of the invention is further a mail piece with a mail piece envelope, which is provided with a flap equipped with a gumming, which by using a sealing liquid according to the invention is sealed by wetting the gumming, folding the flap and pressing the gumming against the mail piece envelope. The safety additive is arranged with a defined laterally inhomogeneous distribution in the section of the gumming.

The kit according to the invention may be part of a semi-automatic or fully automatic device, which closes a mail piece. In such an automated device the closing of the mail piece may be executed by application of the above-described sealing liquid with the above described means for application of such sealing liquid to the mail piece to be closed and by closing the same. In a second device (which may be realized as a further component of a combined device) an automated detection of the lateral distribution of the safety additive in a mail piece may be realized. In this case an automated alarm signal may be created, in case that a mail piece is identified which, after analysis of the lateral distribution of the safety additive is identified as already opened.

The kit according to the invention may also be offered for manual application. In this case a roll, a stamp or a sponge may be wetted with a sealing liquid according to the description above which will be applied to the mail piece manually. Also the detection may be carried out manually, for example by the use of a luminescent dye in combination with a UV-lamp.

Finally, the invention relates to a method for detecting an unauthorized opening of a mail piece sealed by a method according to the invention, wherein the laterally inhomogeneous distribution of the safety additive is detected and/or indicated and optionally automatically compared to a laterally inhomogeneous reference distribution. With respect to the detection, the sealing liquid, and the device for application of the sealing liquid reference is made to the above explanations with regard to different safety additives.

DESCRIPTION OF THE INVENTION

In the following, the invention is described in more detail with reference to embodiments representing examples of execution only.

Example 1

Sealing Liquids According to the Invention

The following commercially available sealing liquids can for instance be used as sealing liquids: sealing liquid "FT" of the company FrancoTech GmbH, Germany, "E-Z Seal" of the company Pitney Bowes, USA and "Quick Seal" preparation of the company Service Industries, USA, in the form as sold in Canada.

Further, sealing liquids can be used, which contain aqueous solutions with a penetration agent and auxiliary agents. As penetration agents can be used: EGDA (ethylene glycol diacetate), DEGMEE (diethylene glycol monoethylether), EL (ethyl lactate) and EGMBE (ethylene glycol monobutylether). All these substances are obtainable from the company Merck, Germany. As auxiliary agents can be used: NaLac (sodium lactate solution 50%, Merck, Germany), TMN 6 (Tergitol TMN 6 non-ionic tenside, Fluka, Germany), AM R 40 (ricinoleic amino propyl betaine, amphoteric tenside sample, Degussa, Germany) and acid rhodamine BC 01 as a dye (Duasyn Merck).

To a sealing liquid mentioned above, a usual, commercially available fluorescent substance is added, which has in the visible range, at least for the concentration used here, no color detectable by the human eye, however lights up under irradiation by a UV lamp in a red color. The addition is made with approx. 0.01 wt.-%.

Example 2

Applying a Sealing Liquid According to Example 1

The gumming of a letter envelope is wetted by a wetting sponge provided for a letter-closing device with sealing liquid according to Example 1. The wetting sponge contains a plurality, for instance 5, square recesses of a size of 2×2 mm, which are uniformly lined up in distances of 5 mm between the squares along the longitudinal extension of the wetting sponge and thus along the longitudinal extension of the gumming to be wetted. Thereby are formed corresponding sections of the gumming, which are not wetted. Then the flap is folded and pressed against the letter envelope.

Example 3

Testing a Mail Piece Having been Sealed According to Example 2 and Opened in a not Unauthorized Manner The letter envelope is first slit open by a letter opener along an edge. Then the inner side of the letter envelope is irradiated by a UV lamp. In the section of the letter envelope, on which the flap with the gumming has been folded (and still adheres), under the UV irradiation a red shining surface can be seen, which is interrupted by approximately square gaps. This can be seen on the inner side, since the sealing liquid is absorbed by the letter envelope when sealing it. Thereby, only a slight washing-out of the pattern in the plane of the gumming occurs. The observation shows as a result that the letter envelope has not been opened. This can be automated by recording the pattern for instance by a CCD camera and comparing it to a reference pattern. In case of a positive comparison, a display "OK" or the like may take place. In case of a negative comparison, an alarm signal is generated, optically and/or acoustically.

Example 4

Testing a Mail Piece Having been Sealed According to Example 2 and Opened in a not Unauthorized Manner First, a letter envelope is sealed according to Example 3. Then the letter envelope is exposed in the section of the gumming to a water vapor atmosphere, until the flap can be opened without destruction. Thereafter, the flap, if necessary after another wetting, is closed again. Then the letter envelope is opened and inspected according to Example 3. A nearly uniform distribution of the red shining safety additive appears, and the mail piece can be qualified as having been opened in an unauthorized manner.

This results is based on that the opening in a water vapor atmosphere leads to strong washing-out of the safety additive and that a precise re-closure at exactly the same position of the flap is very difficult. As a result, by opening and re-closing, the pattern is irreversibly destroyed. The unauthorized person has however not noticed this, since the safety additive cannot be seen in visible light.

Example 5

Manual Application of a Sealing Liquid According to Example 1.

The gumming of an envelope is wetted with a roller, the roller being wetted with a sealing liquid according to example 1. The roller contains a plurality of wave-like depressions with a width of 2 mm each. By a simple manual rolling of the gummed area of the envelope a wave-like pattern is created where the gumming is not wetted. Then the flap is folded and pressed against the letter envelope.

Example 6

Testing a Mail Piece which has been Sealed According to Example 5 and Opened in an Unauthorized Manner.

A letter is sealed according to example 5. Then the envelope will be treated with water vapor in the area of the gumming until the flap may be opened in a non-destructive manner. Subsequently the flap will be closed again, optionally by a further wetting. The envelope will be opened according to example 3 and inspected. A more or less uniform distribution of the red shining safety additive appears, and the mail piece can be qualified as having been opened in an unauthorized manner.

Figure 1:
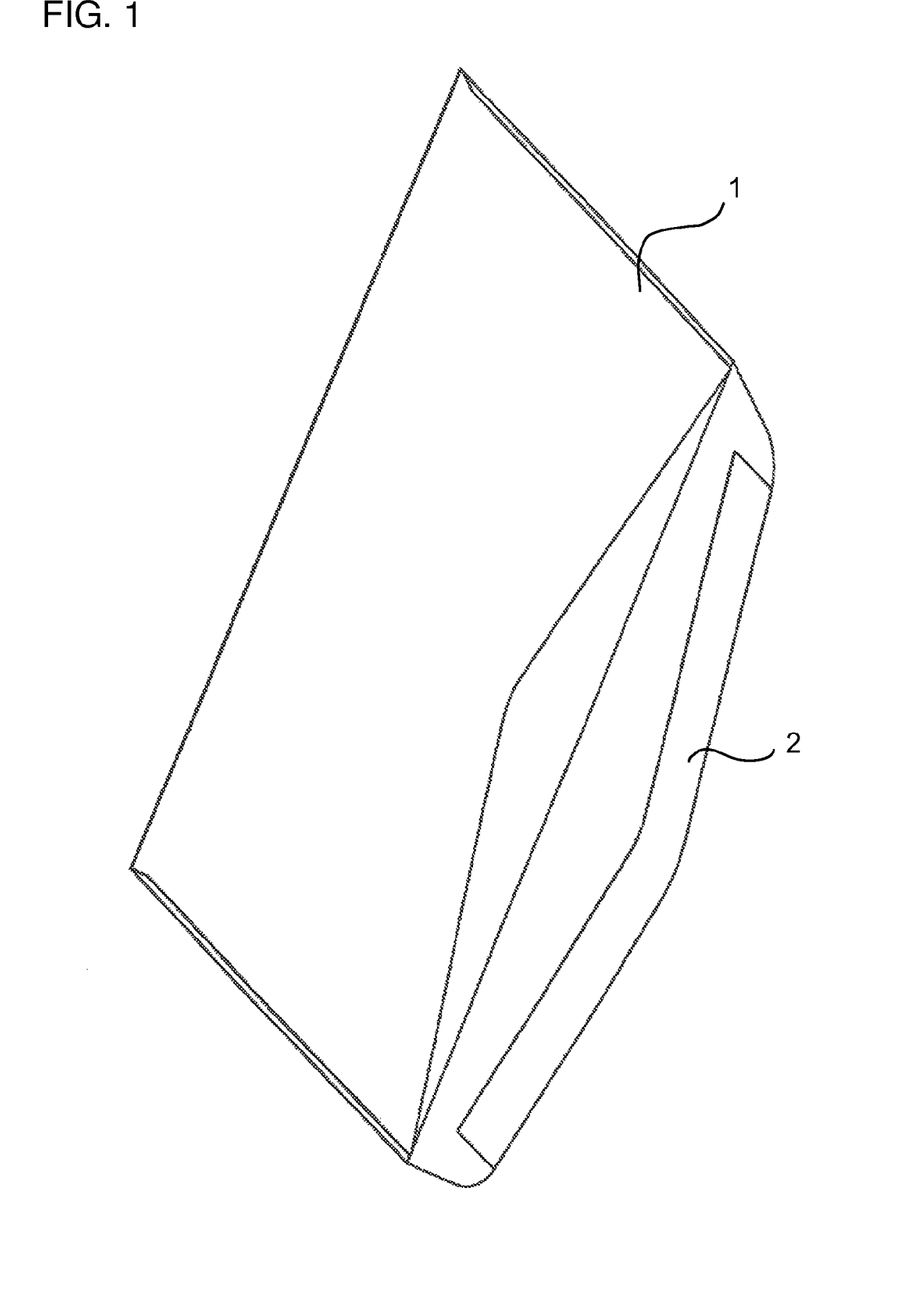
FIG. 1 is an illustration of an envelope with a gummed flap.

As an example, an envelope 1 with a gummed flap 2 is shown in FIG. 1.

Figure 2:
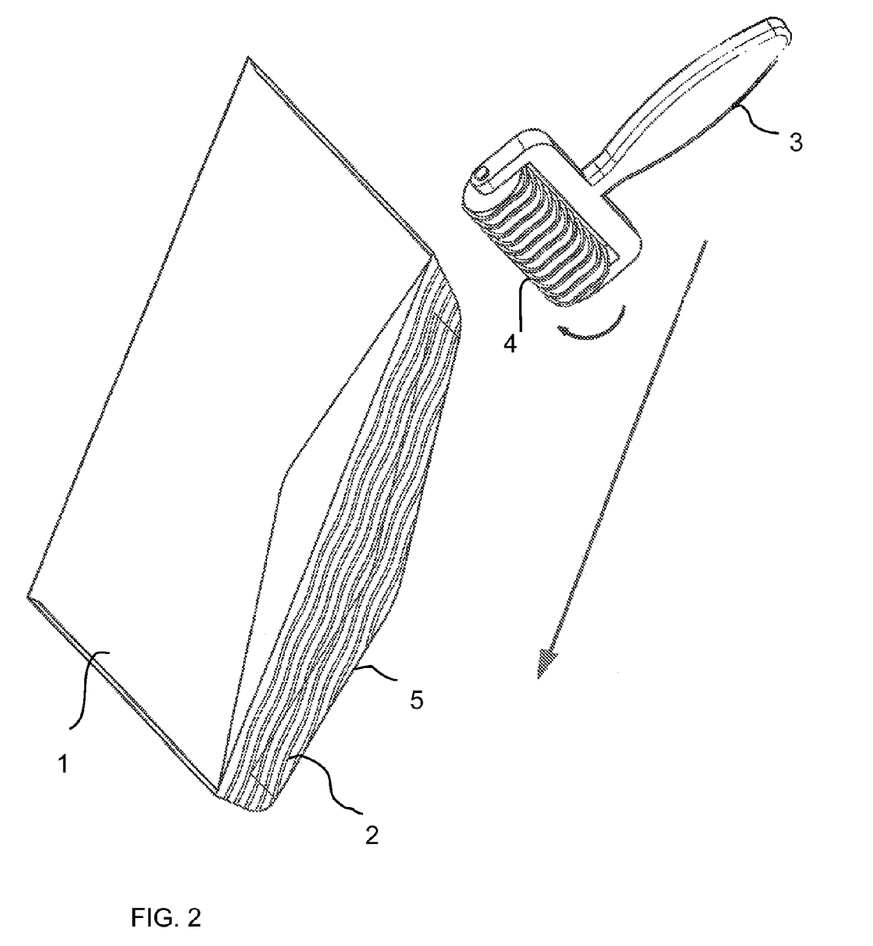
FIG. 2 is an illustration of a roller with wave-like depressions for the creation of a wave-like pattern on gumming of the envelope according to the invention.

FIG. 2 shows a roller 3 with wave-like depressions 4 for the creation of a wave-like pattern 5 on the gumming 2 of the envelope 1.

Figure 3:
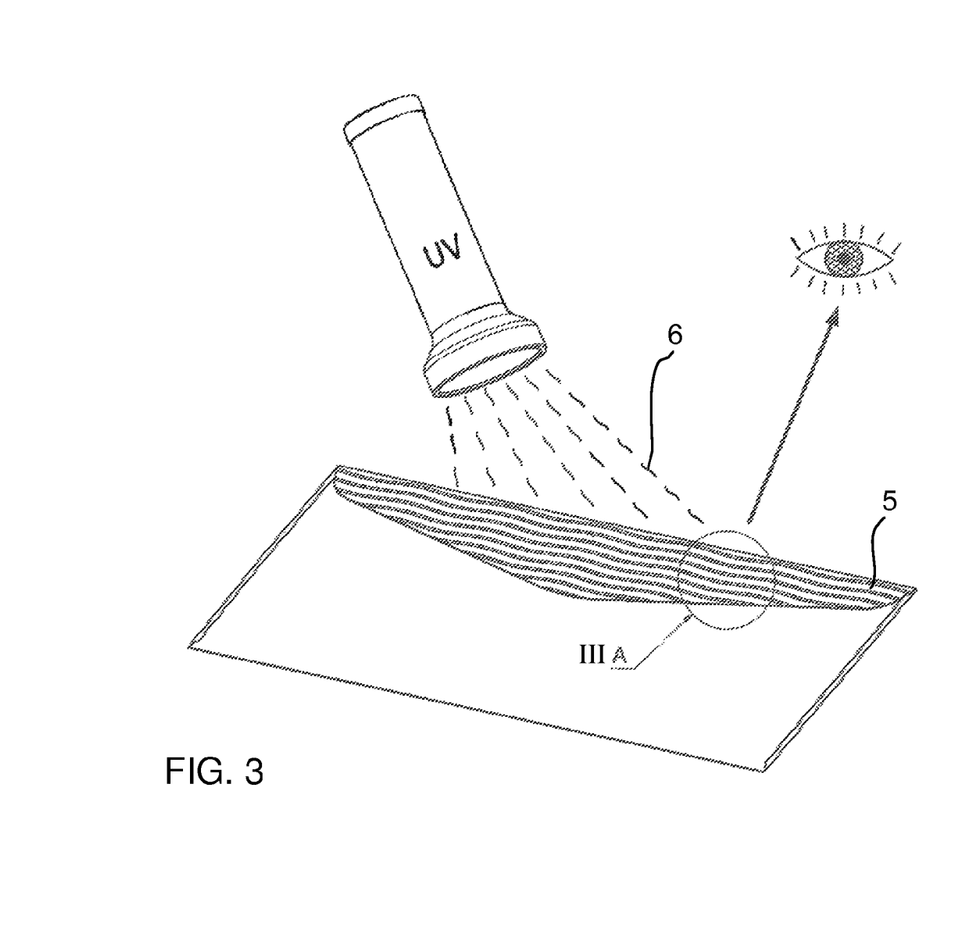
FIG. 3 is an illustration of a created pattern being visible by (e.g.) UV-radiation.
Figure 3A:
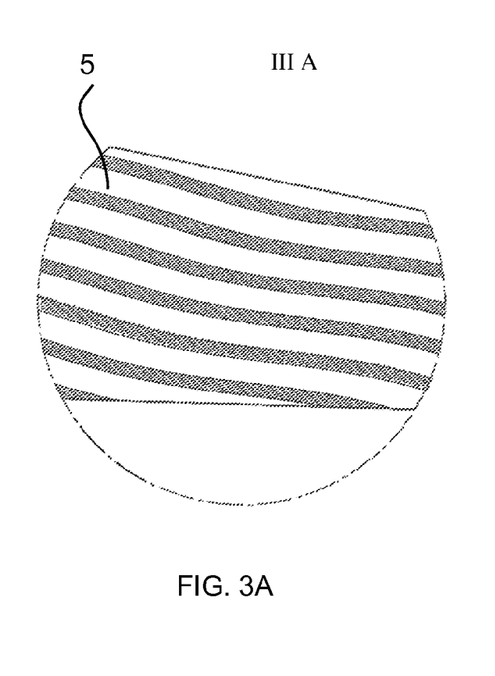
FIG. 3A is an illustration of a detail from FIG. 3 showing a wave-like distribution of the created pattern.

The created pattern 5 being visible by (e.g.) UV-radiation 6 is shown in FIG. 3. Detail IIIA shows the wave-like distribution of the pattern in very sharp lines, see FIG. 3A.

Figure 4:
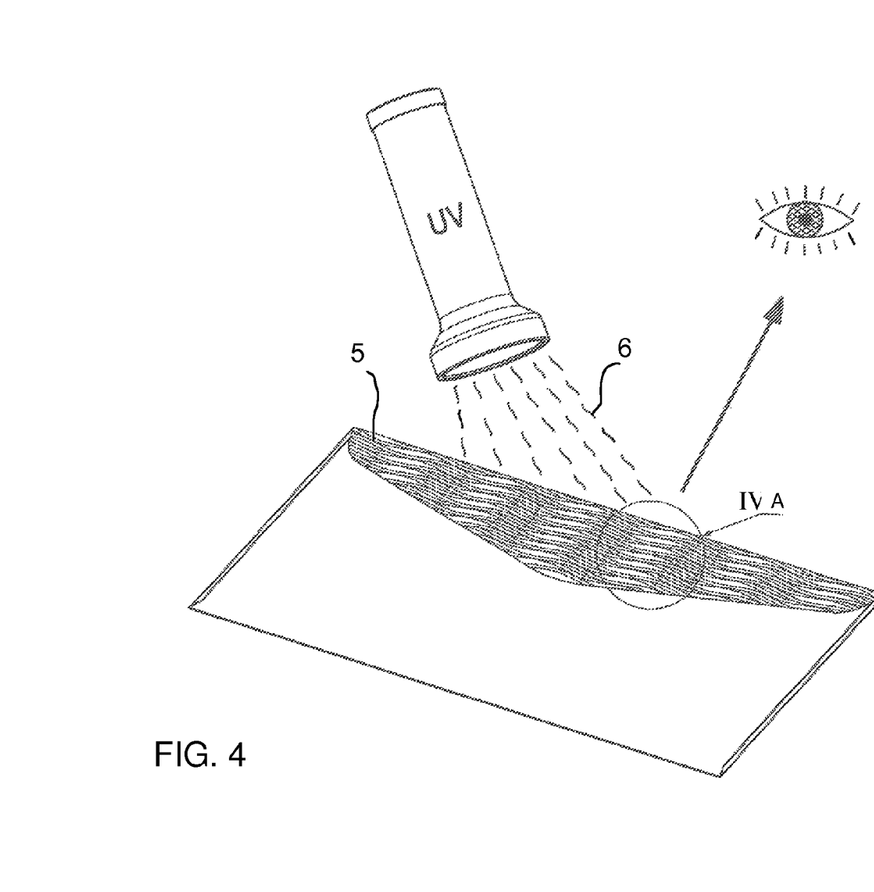
FIG. 4 is an illustration of the created pattern being visible by UV-radiation, after an unauthorized opening.
Figure 4A:
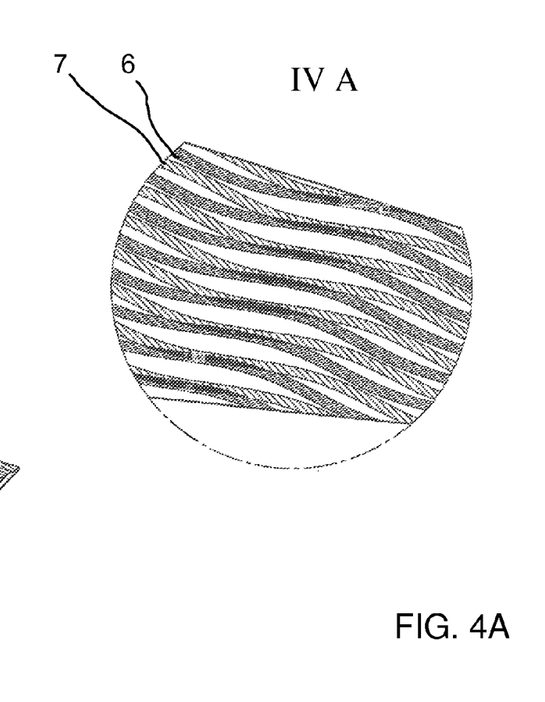
FIG. 4A is an illustration of a detail from FIG. 4 of the unauthorized opening.

FIG. 4 shows the created pattern 5 being visible by UV-radiation 6, after an unauthorized opening. In this example the unauthorized opening did not lead to a complete blurring of the safety additive. However, it is impossible by any attempt to re-close the envelope 1 to place the wave lines exactly on another. As a result a kind of interference pattern 7 is created, since the created wave like pattern on the flap does not match the wave-like pattern on the body of the envelope 1. Such interference pattern 7 is an evidence for unauthorized opening of the letter. FIG. 4A shows detail IVA of the wave pattern after the unauthorized opening.

Figure 5:
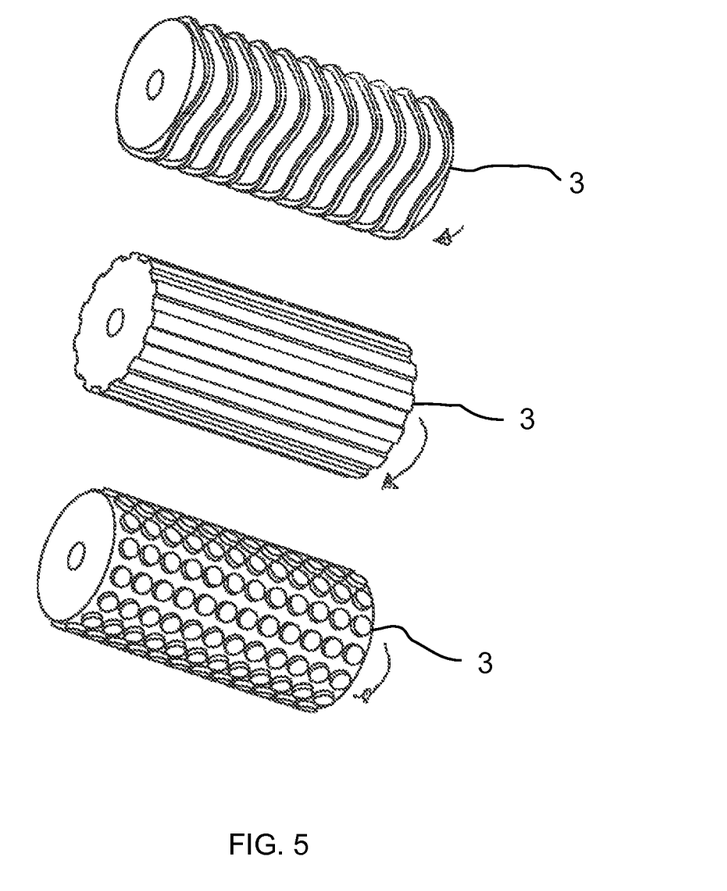
FIG. 5 is a diagrammatic, perspective view of various kinds of rollers for the application of the sealing liquid on gumming of the envelope.

Various kinds of rollers 4 for applying the sealing liquid on gumming of the envelope are shown in FIG. 5. Such rollers 3 may be used manually or be part of a machine, such as a franking machine.

Figure 6:
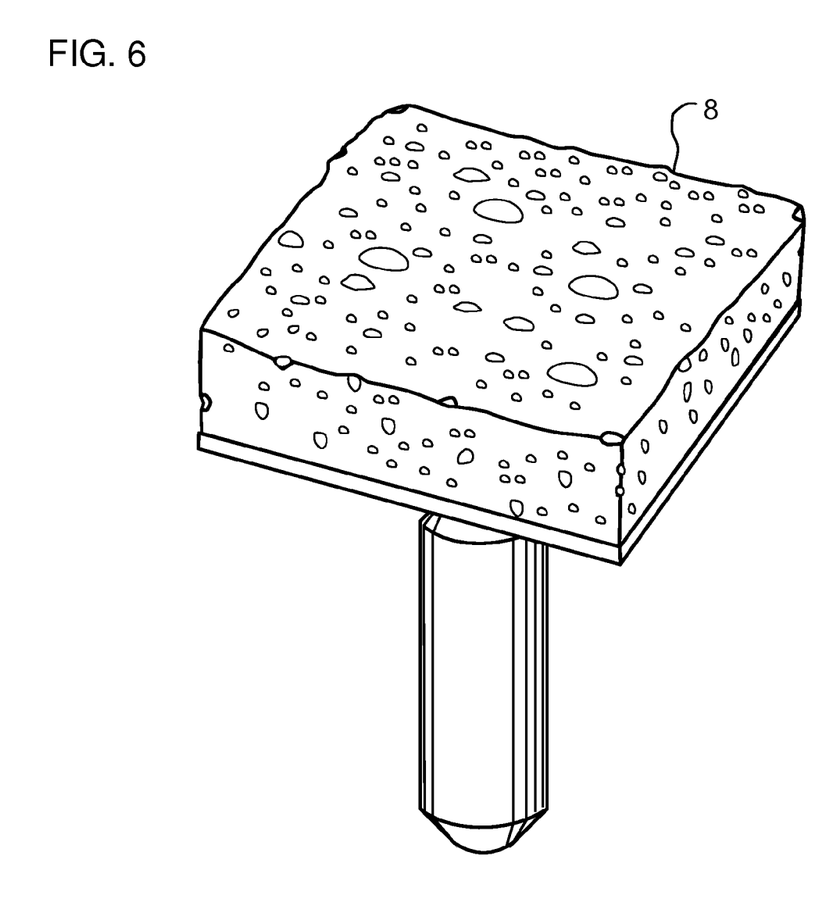
FIG. 6 is a diagrammatic, perspective view of a stamp for the application of the sealing liquid.

FIG. 6 shows a stamp 8 for the application of the sealing liquid. The stamp 8 contains the surface of a sponge. The application of the sealing liquid with such a sponge creates an erratic pattern. Nevertheless the unauthorized opening of a mail piece may also be detected fast without any doubt.

The invention claimed is:

1. A kit for detecting an unauthorized opening of a mail piece, the kit comprising:
   at least one sealing liquid for sealing mail pieces and containing water and a safety additive not being visible by immediate observation;
   at least one device for application of said sealing liquid to the mail piece, said at least one device including a surface having a pattern thereon, said pattern configured to apply a defined lateral inhomogeneous distribution of said sealing liquid to the mail piece; and
   at least one further device for a visualization of said safety additive.

2. The kit according to claim 1, wherein said safety additive is selected from the group consisting of luminescent substances, peptides, proteins, nucleic acids, nucleic acids with 2 to 50 nucleotides, low-molecular inorganic and organic substances different from other components of said sealing liquid.

3. The kit according to claim 1, wherein said sealing liquid contains:
   a) 50 to 99.9 wt.-% of said water;
   b) 0 to 10.0 wt.-% penetration agent;
   c) 0 to 10.0 wt.-% wetting agent;
   d) 0 to 10.0 wt.-% of at least one of a stabilizer or a buffer;
   e) 0 to 5.0 wt.-% dyes;
   f) 0 to 5.0 wt.-% aromatic substances;
   g) 0 to 10.0 wt.-% of at least one of biocides, fungicides or other usual auxiliary substances;
   h) 0.0001 to 10.0 wt.-% of said safety additive; and
   wherein said components a) to h) always add up to 100 wt.-%.

4. The kit according to claim 1, wherein said device for application of said sealing liquid to the mail piece is selected from the group consisting of a roller, a stamp, and a sponge.

5. The kit according to claim 4, wherein said device for application of said sealing liquid to the mail piece applies said sealing liquid manually.

6. The kit according to claim 1, wherein said further device for the visualization of said safety additive is selected from the group consisting of a UV-lamp and a CCD camera.

7. The kit according to claim 1, wherein said sealing liquid contains:
   a) 70 to 99.0 wt.-% of said water;
   b) 1.0 to 30.0 wt.-% penetration agent;
   c) 0 to 3.0 wt.-% wetting agent;
   d) 0 to 3.0 wt.-% of at least one of a stabilizer or a buffer;
   e) 0 to 2.0 wt.-% dyes;
   f) 0 to 1.0 wt.-% aromatic substances;
   g) 0 to 1.0 wt.-% of at least one of biocides, fungicides, other usual auxiliary substances;
   h) 0.0001 to 2.0 wt.-% of said safety additive; and wherein said components a) to h) always add up to 100 wt.-%.

8. The kit according to claim 1, wherein said sealing liquid contains:
   a) 80 to 99.0 wt.-% of said water;
   b) 1.0 to 20 wt.-% penetration agent;
   c) 0.01 to 1.0 wt.-% wetting agent;
   d) 0.01 to 2.0 wt.-% of at least one of a stabilizer or a buffer;
   e) 0.01 to 1.0 wt.-% dyes;
   f) 0.01 to 0.1 wt.-% aromatic substances;
   g) 0 to 0.1 wt.-% of at least one of biocides, fungicides or other usual auxiliary substances;
   h) 0.0001 to 0.1, wt.-% of said safety additive; and
   wherein said components a) to h) always add up to 100 wt.-%.

9. The kit of claim 1, wherein said pattern is a geometrical pattern.

10. A kit for detecting an unauthorized opening of a mail piece, the kit comprising:
   at least one sealing liquid for sealing mail pieces and containing water and a safety additive not being visible by immediate observation;
   at least one device configured to apply said sealing liquid to the mail piece with a defined lateral inhomogeneous distribution and to automatically close said mail piece over said applied sealing liquid; and
   at least one further device for a visualization of said safety additive.

* * * * *